(12) United States Patent
Hao et al.

(10) Patent No.: US 9,081,998 B2
(45) Date of Patent: Jul. 14, 2015

(54) METHOD FOR UTILIZING SOFT X-RAY MICROIMAGING FOR CANCER CELL IMAGE RECOGNITION

(75) Inventors: Jian Hao, Hangzhou (CN); Fan Zhang, Hefei (CN); Maosheng Dong, Hangzhou (CN); Yi Luo, Hangzhou (CN); Sheng Wu, Hangzhou (CN); Yongfei Zhao, Hangzhou (CN); Bo Wang, Hangzhou (CN)

(73) Assignee: No. 128 Hospital of Hangzhou, Hangzhou (CN)

( * ) Notice: Subject to any disclaimer, the term of this patent is extended or adjusted under 35 U.S.C. 154(b) by 277 days.

(21) Appl. No.: 13/699,116

(22) PCT Filed: May 9, 2011

(86) PCT No.: PCT/CN2011/073800
§ 371 (c)(1),
(2), (4) Date: Nov. 20, 2012

(87) PCT Pub. No.: WO2012/139313
PCT Pub. Date: Oct. 18, 2012

(65) Prior Publication Data
US 2013/0071876 A1    Mar. 21, 2013

(30) Foreign Application Priority Data
May 3, 2011    (CN) .......................... 2011 1 0112177

(51) Int. Cl.
*G06K 9/00* (2006.01)
*G01N 23/04* (2006.01)
(52) U.S. Cl.
CPC ............ *G06K 9/00127* (2013.01); *G01N 23/04* (2013.01)

(58) Field of Classification Search
None
See application file for complete search history.

(56) References Cited

U.S. PATENT DOCUMENTS 4,979,203 A * 12/1990 Suckewer et al. ............. 378/206
6,287,790 B1 * 9/2001 Lelievre et al. ............. 435/7.23
(Continued)

FOREIGN PATENT DOCUMENTS

| CN | 1462884 A | 12/2003 |
|----|-----------|---------|
| CN | 1564046 A | 1/2005 |

(Continued)

OTHER PUBLICATIONS

Kirz et al., Soft X-Ray Microscopes and their Biological Applications, Q. Rev. Biophys, 1995, pp. 1-100, vol. 28, No. 1.
(Continued)

*Primary Examiner* — Shervin Nakhjavan
(74) *Attorney, Agent, or Firm* — The Webb Law Firm

(57) ABSTRACT

This invention discloses a method for utilizing soft X-ray microimaging for cancer cell image recognition. The method comprises the steps of 1) sample preparation; 2) pathological examination; 3) soft X-ray imaging; and 4) analysis and recognition. This invention applies soft X-ray microimaging for cancer cell image recognition, successfully obtains the soft X-ray microscopic image of a cancer cell by scanning the cancer cell with synchrotron radiation soft X-ray microimaging, provides recognition steps and experimental data, and establishes a method for utilizing soft X-ray microimaging for cancer cell image recognition. This invention creates a method for analyzing soft X-ray microscopic images, provides a novel synchrotron radiation soft X-ray pathological diagnosis method for cancer diagnosis, and provides an extremely valuable basis for the creation and clinical application of soft X-ray pathology in the 21$^{st}$ century.

2 Claims, 14 Drawing Sheets

(56) References Cited

U.S. PATENT DOCUMENTS

| | | | |
|---|---|---|---|
| 8,506,558 B2* | 8/2013 | Gertner et al. | 606/4 |
| 2007/0082062 A1* | 4/2007 | LeGeros | 424/602 |
| 2010/0002929 A1 | 1/2010 | Sammak et al. | |
| 2013/0303456 A1* | 11/2013 | Van Meir | 514/13.3 |

FOREIGN PATENT DOCUMENTS

| | | |
|---|---|---|
| CN | 1624475 A | 6/2005 |
| CN | 1746901 A | 3/2006 |
| CN | 101164551 A | 4/2008 |

OTHER PUBLICATIONS

Feder, et al., Direct Imaging of Live Human Platelets by Flash X-Ray Microscopy, Science, 1985, pp. 63-64, vol. 227.

Shinohara et al., X-Ray Holographic Microscopy of Biological Specimens with an Electronic Zooming Tube, Journal of Synchrotron Radiation, 1996, pp. 35-40, vol. 3.

* cited by examiner

METHOD FOR UTILIZING SOFT X-RAY MICROIMAGING FOR CANCER CELL IMAGE RECOGNITION

FIELD OF THE INVENTION

This invention relates to a method for utilizing soft X-ray microimaging for cancer cell image recognition.

PRIOR ART

First discovered by Roentgen in 1895, X-ray was superior in penetrating substances and suitable for the imaging of human tissues and organs. X-ray has a relatively short wavelength, ranging from 0.1 to 1.0 nm. However, the complexity in interaction between X-ray and substances and the difficulty in the manufacture of optical components in applications similar to visible light make it hard to devise an X-ray microscope. The electron positron collision synchrotron radiation light source emits special soft X-ray with a wavelength ranging from 1 to 10 nm, which can be converged and projected on a sample through optical diffractive concentration and optical components before being imaged on an image plane.

Soft X-ray microimaging has a resolution of 10 nm, and its principle is as follows:

a sample is appressed onto a detector (photoresist) sensitive to soft X-ray. After exposure and "development" of soft X-ray, a photoresist-radiated image appears which corresponds to the shape of the original sample. Then an optical or electron microscope is used to observe this image to obtain the soft X-ray microscopic image of the sample.

Soft X-ray microscopy is a microimaging technology which mainly uses soft X-ray in the "water window" waveband (2.3-4.4 nm) as a light source. Compared with an optical microscope, it has higher imaging resolution; compared with an electron microscope, it features simple sample preparation—ultra thin sliced samples without traditional pathological examination procedures such as freezing, wax sealing, dehydration and dyeing. To sum up, soft X-ray microimaging can observe the submicroscopic morphological characteristics of cell tissues without the traditional pathological method.

In recent years, the applied research of soft X-ray microscopy has made headway, especially in the field of life science. Besides similar pathological diagnosis values, soft X-ray microimaging has the following characteristics: ① identifiability is realized without dyeing, and its resolution (70.0 nm) is higher than that of the optical microscope and in the neighborhood of that of the electron microscope; ② an issue sample can be subject to pathological examination and analysis when alive; ③ the submicroscopic structure of an invivo tissue cell in a natural state can be subject to differential diagnosis, and soft X-ray microimaging can be applied in clinical diagnosis. A soft X-ray microscope can observe biological samples in the natural state. At present, it can not only observe the ultramicroscopic structure and internal dynamic changes of a cell, but also study the distribution of protein, DNA or any other biological macromolecules on samples at the cellular level.

Soft X-ray microscopy has paved a new path for biomedical research, and commanded attention from global scientists. This technology has rapidly developed worldwide as it is most suitable for high-resolution imaging of biological samples in the natural state. Many countries have made substantial headway in developing various kinds of soft X-ray microscopes and applying them in the study of biomedical samples.

Many countries, such as US, Russia, German, Japan, UK and France, have mastered this technology, and implemented researches on the application of soft X-ray in biomedical samples. At 1981 Brookhaven and 1983 GÖttingen meetings, Kirz and Rarback released summary reports on soft X-ray. In 1985, Feder et al. successfully obtained the soft X-ray microscopic image of an invivo blood platelet at a resolution of about 10 nm with the soft X-ray microimaging method; in 1990, Shinohara et al. shot the clear soft X-ray microscopic image of a HeLa cell nucleolus, and observed and analyzed the structures of chromatin and zymogen granules. Nonetheless, there have been no foreign reports of soft X-ray microscopy applied in clinical medicine, or X-ray microimaging and computer neural network intelligentization soft X-ray pathological diagnosis technology performed to the submicroscopic structure of cancer cells.

Despite not being an early adopter of soft X-ray microimaging, China emerged as one of the forerunners, and attached greater importance to the research and application of soft X-ray microimaging. Completed in 1991, the National Synchrotron Radiation Laboratory (NSRL), located in the University of Science and Technology of China (USTC) in Hefei, Anhui province, has been open to domestic and foreign researchers since 1992. Domestic researchers and scholars have made outstanding contributions to the theory and practice of soft X-ray microscopy, as part of their efforts to study soft X-ray microscopy on the Hefei Light Source, which also yielded many results. USTC Prof. Xie Xingshu made great contributions to the theory and practice of soft X-ray microscopy. Some scholars applied soft X-ray imaging in studying *E. coli*, men's sperms and insect wings, etc.

In China, soft X-ray microimaging is more applied frequently in microbiology and biological samples of plants and animals. However, there have been no domestic and foreign reports of soft X-ray microimaging applied for clinical medicine practices or cancer cell image recognition.

SUMMARY OF THE INVENTION

The purpose of this invention is to provide a method for utilizing soft X-ray microimaging for cancer cell image recognition. This invention applies soft X-ray microimaging for cancer cell image recognition, successfully obtains the soft X-ray microscopic image of a cancer cell by scanning the cancer cell with synchrotron radiation soft X-ray microimaging, provides recognition steps and experimental data, and establishes a method for utilizing soft X-ray microimaging for cancer cell image recognition; this invention creates a method for analyzing soft X-ray microscopic images; provides a novel synchrotron radiation soft X-ray pathological diagnosis method for cancer diagnosis, and provides an extremely valuable basis for the creation and clinical application of soft X-ray pathology in the $21^{st}$ century.

To solve the above-mentioned problems, this invention adopts the following technical scheme:

This invention provides a method for utilizing soft X-ray microimaging for cancer cell image recognition, said method comprises the steps of 1) sample preparation; 2) pathological examination; 3) soft X-ray imaging; and 4) analysis and recognition.

The pathological sample preparation process comprises the following steps:

Step 1: cutting a pathological tissue cell sample into ultra-thin sliced samples with 2-3 nm thickness;

Step 2: placing the ultra-thin sliced samples onto the surface of water in a water tank with 38° C.-40° C. to enable the samples to quickly and uniformly unfold into a planar shape on the water surface;

Step 3: taking out the ultra-thin sliced samples floating and flattening in the water tank with an electron microscope copper grid, and then said grid is placed on a piece of absorbent paper for dehydration and drying.

Said pathological examination comprises the following steps: the electron microscope copper grid ultra-thin sliced samples are sent to a pathological examination department, in where said samples will be subject to a pathological examination under an optical microscope; after a cancer cell is identified, a field of view is selected and fixed for observing the cancer cell; an optical microscopic picture of the cancer cell enlarged by 100 times is shot under the optical microscope.

Said soft X-ray imaging comprises the following steps:

The electron microscope ultra-thin sliced samples are sent to a synchrotron radiation experimental station, in where the samples are subject to scan diffraction by synchrotron radiation soft X-ray microscopic beamlines and imaged on the photoresist, then, microscopic transmission is utilized to observe and shoot a soft X-ray microscopic image.

The wavelength of the soft X-ray microscopic beamlines ranges from 1.0 to 10.0 nm, the water window of soft X-ray microscopy for exposure of biological samples is made of silicon nitride, and has different thickness options, of which the thinnest is 20 nm.

The computer intelligent analysis and recognition comprises the following steps:

After the synchrotron radiation X-ray microscopic imaging of the cancer cell, image signal conditioning is first conducted, image signal collection is then conducted for digital sampling, and finally a digital signal is sent in the form of a serial port or a parallel port into a computer system for processing and intelligent recognition.

The synchrotron radiation soft X-ray microscopic image signal is an analog signal; it must be conditioned by amplification, buffering or calibration before converted to a digital signal, so as to be suitable for being input to a subsequent signal collection unit.

The image signal collection comprises image pre-processing, image segmentation analysis, overlapped cell reconstruction, cell feature extraction, cell feature classification and diagnosis result output.

The image pre-processing comprises grey level transformation, histogram adjustment, cell pre-processing, nucleus pre-processing and lymphocyte removal;

said grey level transformation is a process that utilizes a formula for conversion between a color image and a grey image to convert the cell image to the grey level format, so as to facilitate subsequent processing;

said histogram adjustment is a process that indirectly enhances contrast by stretching or equalizing a histogram;

said cell pre-processing comprises contrast adjustment, binarization and edge detection;

said lymphocyte removal comprises erosion, expansion and logical processing, in order to obtain the image of a cell without lymphocyte;

said image segmentation analysis comprises threshold-based segmentation, structural morphological image processing of cell tissues, and edge detection;

said threshold-based segmentation is for cell outline segmentation;

said structural morphological image processing of cell tissues involves outline tracking, erosion and expansion;

said edge detection eliminates noise caused by inter-cell adjacency, lest the subsequent extraction of cell feature values is affected;

said overlapped cell reconstruction is a process that prevents errors in cytogenesis information extraction caused by pseudo boundaries and outlines obtained by segmentation of interconnected and overlapped cells;

the nucleo-cytoplasmic ratio method or the colorimetric method is adopted for cell feature extraction;

said nucleo-cytoplasmic ratio method uses the bwareaopen function to remove small-area outlines through gradually selecting the thresholds of the areas of connected regions; the outline difference between nucleus and cytoplasm is clearly displayed; the nucleo-cytoplasmic area ratio is calculated; for normal cells, the nucleo-cytoplasmic ratio is 1:4 or 1:6; for cancer cells, the ratio is 1:1;

said colorimetric method utilizes the colorimetric characteristics of cancer cell nucleus for further classification and recognition of suspected cancer cell nucleus, given that cancer cell nucleus is normally darker than normal cell nucleus and the clustering of its color components varies in a color space;

said cell feature classification and diagnosis result output method includes the BP neural network method, the support vector machine method or the decision tree method;

said BP neural network method utilizes three layers of BP network for cancer cell diagnosis, and involves extracting feature parameters according to the clinical features of a cancer cell, collecting a large number of samples to train neural networks, and utilizing trained networks for cancer cell diagnosis.

The cancer cell in this invention is the esophageal carcinoma cell or lung cancer cell of human beings.

This invention applies soft X-ray microimaging for cancer cell image recognition, successfully obtains the soft X-ray microscopic image of a cancer cell by scanning the cancer cell with synchrotron radiation soft X-ray microimaging, provides recognition steps and experimental data, and establishes a method for utilizing soft X-ray microimaging for cancer cell image recognition;. this invention creates a method for analyzing soft X-ray microscopic images, provides a novel synchrotron radiation soft X-ray pathological diagnosis method for cancer diagnosis, and provides an extremely valuable basis for the creation and clinical application of soft X-ray pathology in the $21^{st}$ century.

BRIEF DESCRIPTION OF THE DRAWINGS

FIG. 9-1 is the diagram of using the Laplacian operator for edge detection.

FIG. 9-2 is the diagram of using the Roberts operator for edge detection.

FIG. 9-3 is the diagram of using the Sobel operator for edge detection.

FIG. 9-4 is the diagram of using the Prewit operator for edge detection.

DETAILED DESCRIPTION OF EMBODIMENTS

Embodiment 1

Figure 1:
FIG. 1 is the original data of soft X-ray microimaging of an esophageal squamous carcinoma cell.

Method for Utilizing Soft X-Ray Microimaging for Esophageal Squamous Carcinoma Cell Image Recognition 6 hospitalized patients (4 males and 2 females) suffering esophageal cancer in the age group of 51-64 (57.3 on average) are selected.

Before operation, the patients are subject to fibro-gastroscopic examination. No operation is conducted without pathological confirmation that they suffer esophageal cancer.

Esophageal squamous carcinoma samples are removed and sent to a pathology department to be subject to conventional histological and cytological examinations. After an esophageal squamous carcinoma cell is identified, an optical microscopic picture of the cancer cell enlarged by 100 times is shot under the optical microscope. Meanwhile, the esophageal squamous carcinoma samples are sent to a synchrotron radiation experimental station, where the samples are subject to scan diffraction by soft X-ray microscopic beamlines and imaged on the photoresist. A soft X-ray microscopic image is shot.

Instruments and equipment used in this embodiment include:

Soft X-ray microimaging beamline station, NSRL, USTC; soft X-ray microscopic beamlines with a wavelength ranging from 1.0 to 10.0 nm; the microimaging technology which mainly uses soft X-ray in the "water window" waveband (2.3-4.4 nm) as a light source.

A vacuum drying oven and a CJ-3A photoresist spinner (made by the Beijing Semiconductor Equipment Plant); Olympus differential interference contrast microscope (Japanese), and KYKY-1000B scanning electron microscope (Scientific Instruments Factory of the Chinese Academy of Sciences); 151 II ultramicrotome (SEIXY, West German).

The sample preparation process comprises the following steps:

Step 1: a known esophageal squamous carcinoma cell tissue sample is cut by a German-made pathological ultramicrotome into ultra-thin sliced pathological tissue cell samples with 2-3 nm thickness.

Step 2: the ultra-thin sliced pathological tissue cell samples are placed onto surface of water in a water tank with 38° C.-40° C. to enable the samples to quickly and uniformly unfold into a planar shape on the water surface.

Step 3: a Shanghai-made electron microscope copper grid with a handle is used to take out the ultra-thin sliced pathological tissue cell samples floating and flattening in the water tank, and then said grid is placed on a piece of absorbent paper for dehydration and drying.

The analysis and recognition comprises the following steps: after the synchrotron radiation X-ray microscopic imaging of the cancer cell, image signal conditioning is first conducted, image signal collection is then conducted for digital sampling, and finally a digital signal is sent in the form of a serial port or a parallel port into a computer system for processing and intelligent recognition.

Since a synchrotron radiation soft X-ray microscopic image signal is an analog signal, it must be conditioned by amplification, buffering or calibration before converted to a digital signal, so as to be suitable for being input to a subsequent signal collection unit.

The image signal collection comprises image pre-processing, image segmentation analysis, overlapped cell reconstruction, cell feature extraction, cell feature classification and diagnosis result output.

The image pre-processing comprises grey level transformation, histogram adjustment, etc.; the image segmentation module comprises threshold-based segmentation, structural morphological image processing of cell tissues, edge detection, etc.; the connected region extraction method is adopted for cell feature module extraction; nucleo-cytoplasmic area ratio is adopted for cell feature recognition module determination.

According to Stevens and Lowe's conclusion, cell morphology has such major cytological features as multiple mutation of nucleo-cytoplasmic ratio, nucleus size, nucleus shape, cell size and cell shape and the deep staining of nucleus, which are main bases for studying cytological features. This invention uses nucleo-cytoplasmic ratio as an approach. Nucleo-cytoplasmic ratio means the volume of nucleus vs the volume of cytoplasm in a cell. For a normal cell, the nucleo-cytoplasmic ratio is 1:4 or 1:6. For a cancer cell, the ratio is in the neighborhood of 1:1.

According to the features of esophageal squamous carcinoma cells, this invention explores a method for recognizing cancer cells based on cell area threshold and studies a method for distinguishing normal cells from cancer cells.

Figure 2:
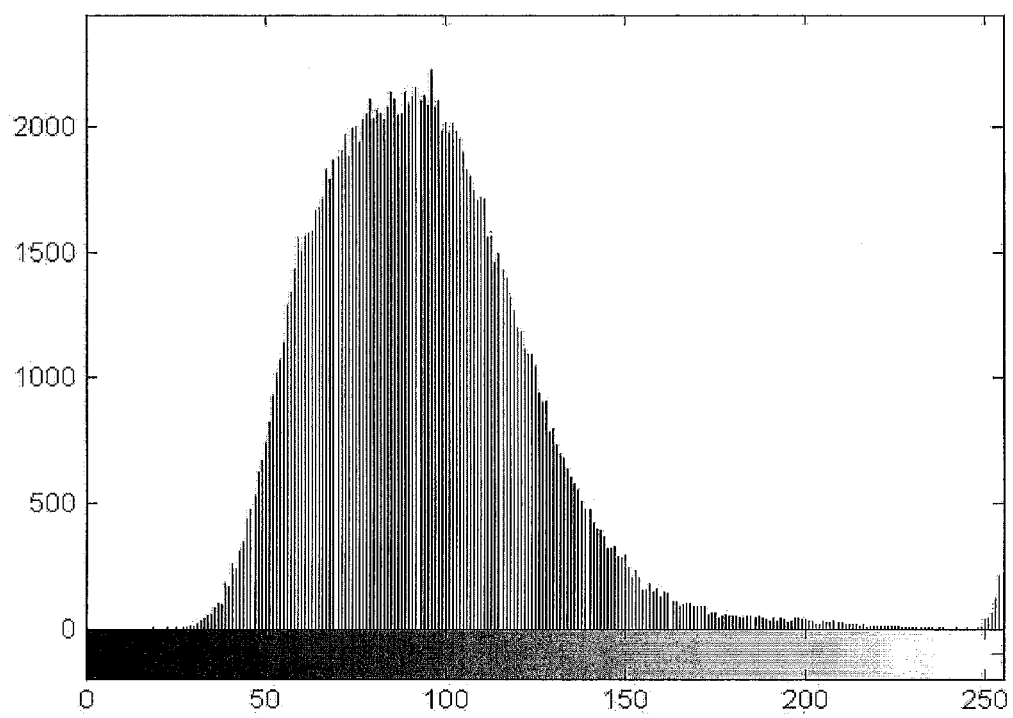
FIG. 2 is the grey level histogram of soft X-ray microimaging of the esophageal squamous carcinoma cell.
Figure 3:
FIG. 3 is the grey level image of the original image of soft X-ray microimaging of the esophageal squamous carcinoma cell.
Figure 4:
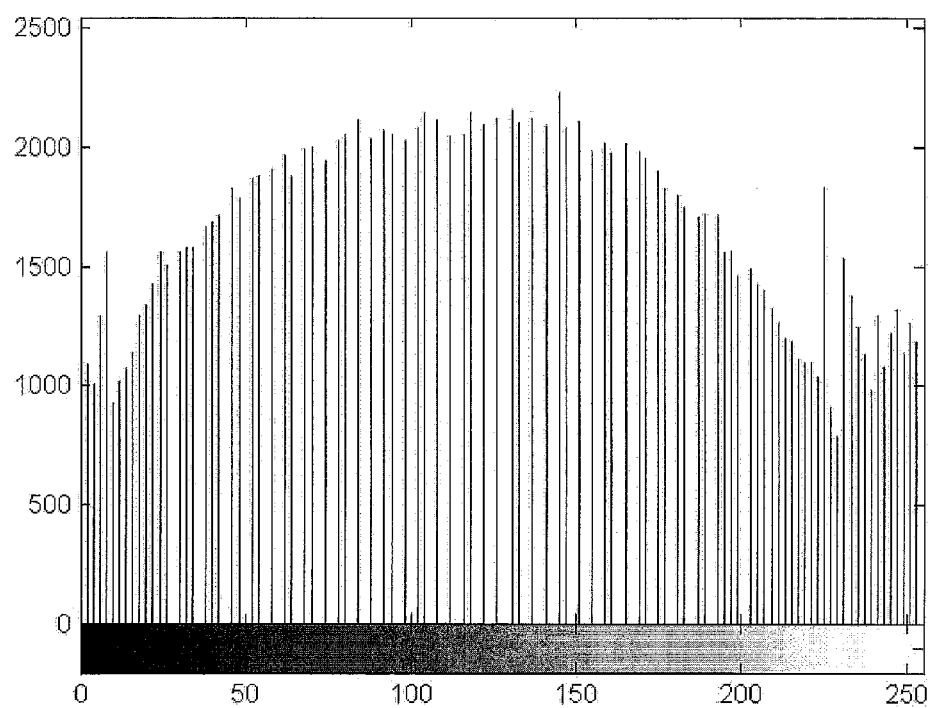
FIG. 4 is the corresponding histogram of FIG. 3.
Figure 5:
FIG. 5 is the grey level transformation diagram of FIG. 3.
Figure 6:
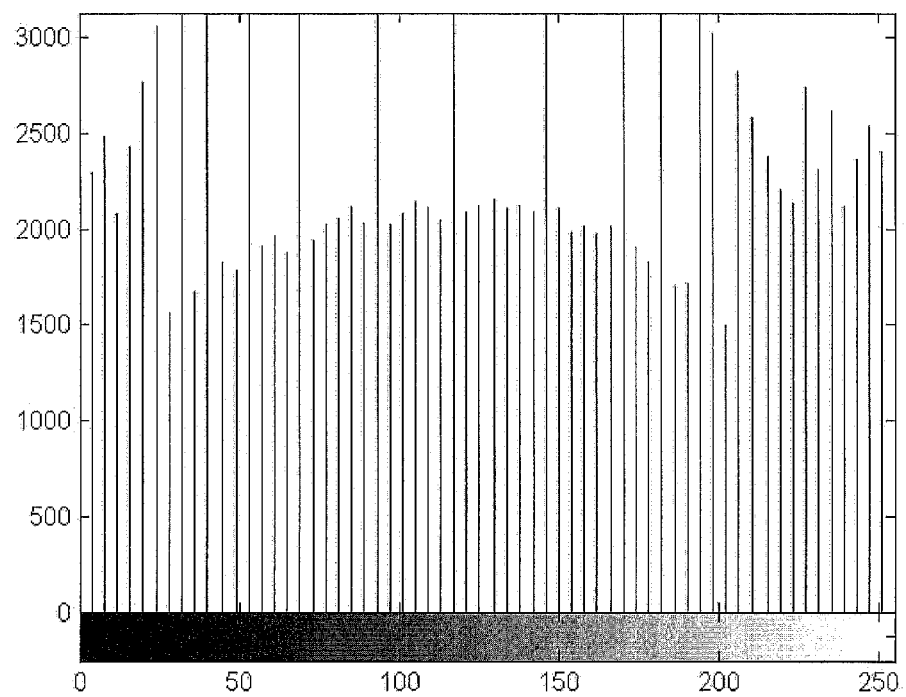
FIG. 6 is the histogram adjustment diagram of FIG. 4.

The original data and grey level histogram of soft X-ray microimaging of the esophageal squamous carcinoma cell are shown in FIG. 1 and FIG. 2, from FIG. 1 and FIG. 2, the nucleolus of the esophageal squamous carcinoma cell is round with clear boundaries and uniform density. Chromatins around the nucleolus are in the shape of large and thick granules or thick and short cable strips. The chromatins are distributed in an oval, a rectangular or an irregular shape with clear boundaries. Cell membranes have clear boundaries and visible micro cracks. The space between the nucleus and the cell membrane is filled with cytoplasm which is uniform in density and in the shape of fine particles.

The image pre-processing comprises grey level transformation, histogram adjustment, etc., as shown in FIG. 3, FIG. 4, FIG. 5 and FIG. 6.

Figure 7:
FIG. 7 shows the image processing of threshold segmentation.
Figure 8:
FIG. 8 shows the image processing of cell morphology.
Figures 1, 9:
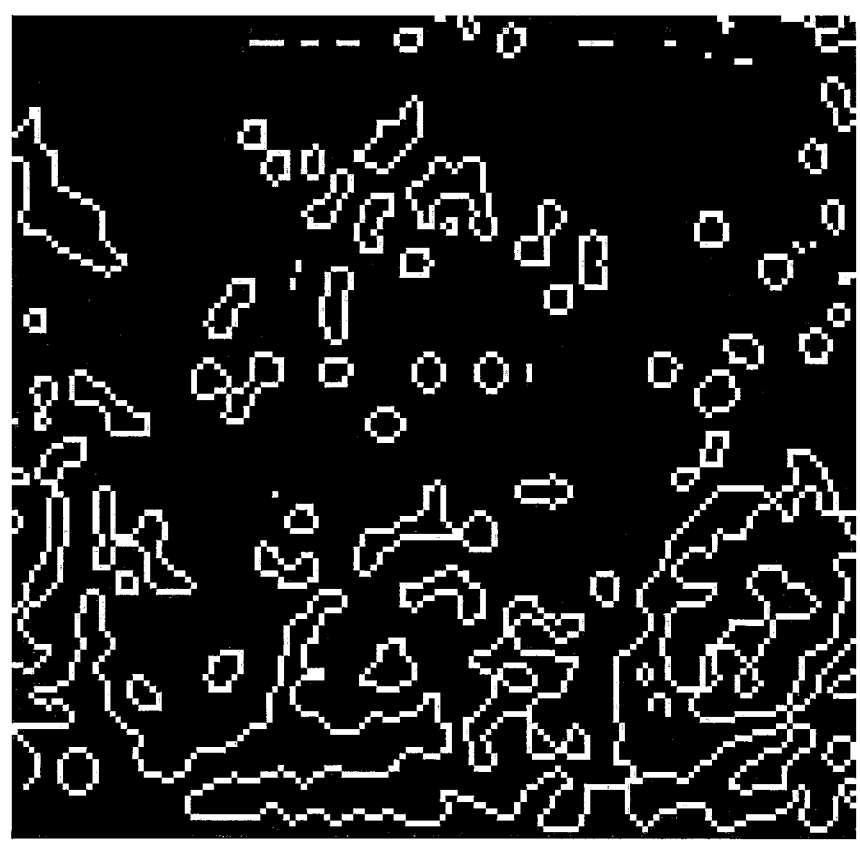
Figures 2, 9:
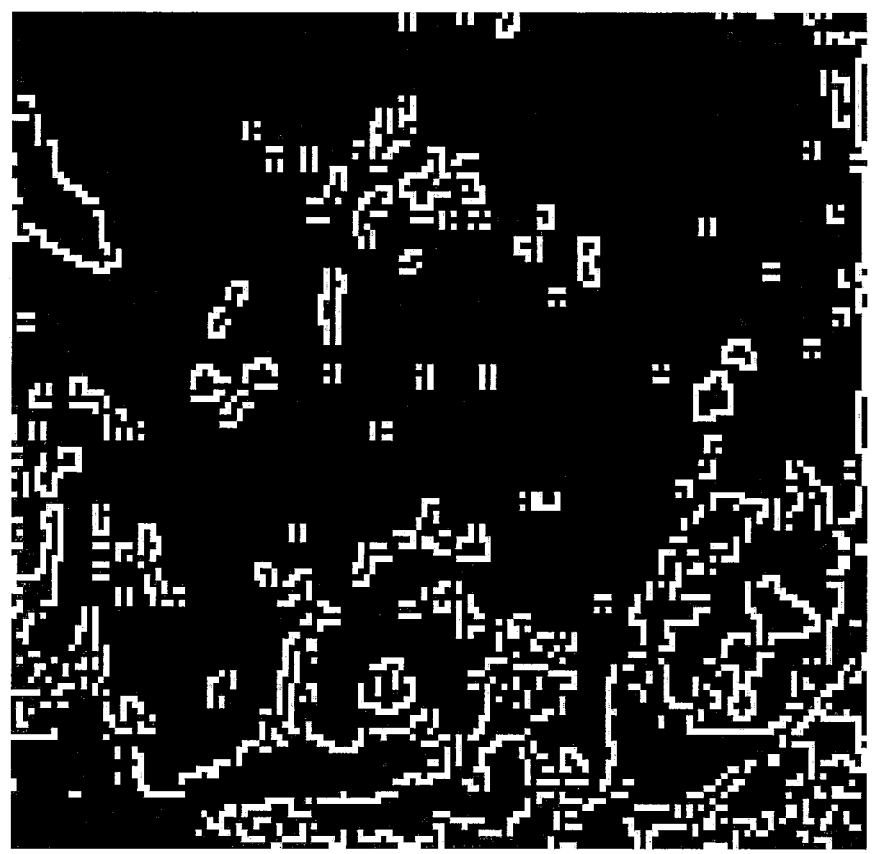
Figures 3, 9:
Figures 4, 9:

The image segmentation begins with threshold segmentation and image processing of cell morphology, as shown in FIG. 7 and FIG. 8.

Then, four common operators, Laplacian, Roberts, Sobel and Prewit, are sequentially adopted for edge detection, as shown in FIG. 9-1, FIG. 9-2, FIG. 9-3, and FIG. 9-4.

Figure 10:
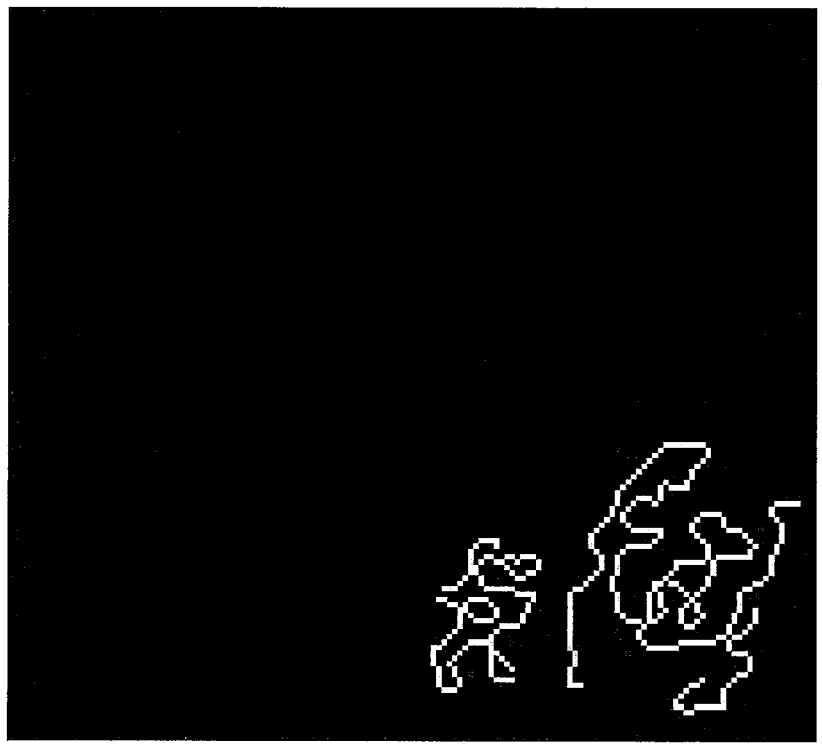
FIG. 10 shows the segmentation of threshold 100.
Figure 11:
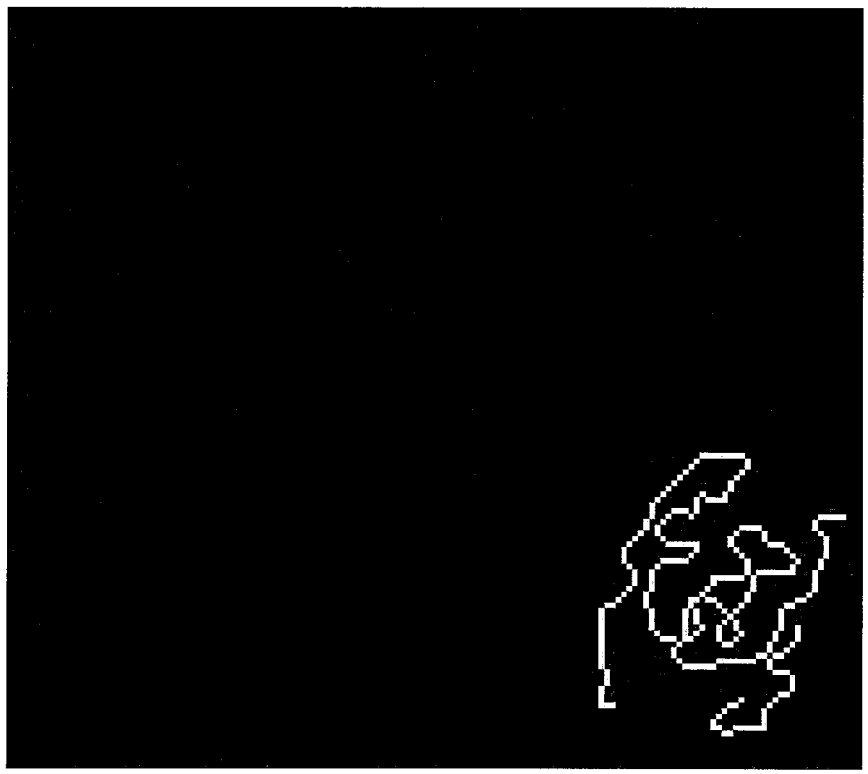
FIG. 11 shows the segmentation of threshold 250.

The connected region extraction method is adopted for cell feature extraction. Firstly, an image corresponding to the Laplacian operator is picked out to calculate the area of connected regions. As a result, too many connected regions are discovered, making it difficult to identify. The bwareaopen function is used to remove small-area outlines through gradually selecting the thresholds of the areas of the connected regions. Finally, thresholds 100 and 250 are selected, as shown in FIG. 10 and FIG. 11 respectively. The benefit of doing so is that the outline difference between nucleus and cytoplasm is clearly displayed.

Segmentation in FIG. 10 results in the formation of one nucleus on the left and one complete cell on the right. Segmentation in FIG. 11 results in the formation of one complete cell on the right.

Nucleo-cytoplasmic area ratio is adopted for cell feature recognition determination.

The results of the calculation of the areas of two regions corresponding to FIG. 10 and the area of one region corresponding to FIG. 11 are as follows:

In FIG. 10, the area of the nucleus on the left is 124, and the total area of the cell on the right is 271 (i.e. sum of nucleus area and cytoplasm area). Based on the principle that neighboring cells are roughly same in area, the cell area on the right, 271, is divided into nucleus area, 124, and cytoplasm area, 147. Therefore, $S_{nucleus}/S_{cytoplasm} \approx 8435$. Based on Stevens and Lowe's theory that $S_{nucleus}/S_{cytoplasm}$ of a normal cell is between 1:6 and 1:4 and $S_{nucleus}/S_{cytoplasm}$ of a cancer cell is in the neighborhood of 1, that means this sample comes from a suspected cancer patient.

The method for utilizing soft X-ray microimaging for cancer cell image recognition has the following advantages:

The resolution of soft X-ray microscopy is determined by the wavelength of used soft X-ray, used photoresist and successive view microscopes. Since soft X-ray can penetrate thick biological substances, the image contrast can be enhanced by changing the wavelength. This invention adopts soft X-ray in the wavelength range of 23-4.4 nm (called "water window"), which have a "transparent" effect on water. Therefore, it is possible to observe thick, hydrous, colorless biological samples in this wavelength range, such as a complete alive cell and the intracellular submicroscopic structure, which are not accessible by an optical microscope or an electron microscope.

The method for recognizing cancer cells based on area threshold according to the features of esophageal squamous carcinoma cells is convenient and simple.

Embodiment 2

Method for Utilizing Soft X-Ray Microimaging for Lung Cancer Cell Image Recognition Lung cancer patients are selected with no gender preference. Selected subjects need to provide their medical history, be subject to physical and lab examinations such as blood routine, liver and kidney function tests, X-ray chest radiography, cancer cells in sputum, and serum tumor marker, as well as soft X-ray imaging examination, and record and summarize results in time.

Bronchofiberscope examination: before operation, selected lung tumor patients are subject to the bronchofiberscope examination. Lung tumor samples are extracted and sent to a pathology department to be subject to conventional histological and cytological examinations. After pathological diagnosis confirms that the patients suffer from lung cancer, the results of pathological diagnosis are specified and promptly recorded and summarized. Specified lung cancer samples are taken as the objects of study and sent to NSRL, USTC where a soft X-ray microimaging sample is prepared for study.

Instruments and equipment include:

Soft X-ray microimaging beamline station (NSRL, USTC);

A vacuum drying oven and a CJ-3A photoresist spinner (Beijing Semiconductor Equipment Plant);

Olympus differential interference contrast microscope (Japan);

KYKY-1000B scanning electron microscope ((Scientific Instruments Factory of the Chinese Academy of Sciences);

151 II ultramicrotome (SEIXY West German).

The preparation of a soft X-ray lung cancer microscopic image:

Step 1: a known lung cancer cell tissue sample is cut by the German-made pathological ultramicrotome into ultra thin sliced pathological tissue cell samples with 2-3 nm thickness.

Step 2: the ultra-thin sliced pathological tissue cell samples are placed on the surface of water in a water tank with 38° C.-40° C. to enable the samples to quickly and uniformly unfold into a planar shape on the water surface.

Step 3: a Shanghai-made electron microscope copper grid with a handle is used to take out the ultra-thin sliced lung cancer tissue cell samples floating and flattening in the water tank, and then said grid is placed on a piece of absorbent paper for dehydration and drying.

Step 4: the electron microscope ultra-thin sliced samples are sent to a pathological examination department, in where to be subject to a pathological examination under an optical microscope; after a cancer cell is identified, a field of view is selected and fixed for observing the cancer cell. An optical microscopic picture of the cancer cell enlarged by 100 times is shot under the optical microscope. Meanwhile, the lung cancer cell samples are sent to a synchrotron radiation experimental station, where the samples are subject to scan diffraction by synchrotron radiation soft X-ray microscopic beamlines and imaged on the photoresist, then, microscopic transmission is utilized to observe and shoot a soft X-ray microscopic image.

Before the soft X-ray imaging examination, said selected subjects should not be subject to any treatments, such as anti-tuberculosis, anti-infection or anti-tumor treatments. All the selected subjects need to be subject to pathological histological and cytological examinations, with pathological diagnosis results as the gold standard.

After the synchrotron radiation X-ray microscopic imaging of the lung cancer cell, an image analog signal is subject to treatments such as preamplification, noise reduction and calibration through a conditioning unit, the signal enters an image collection channel for digital sampling, and finally a digital signal is sent in the form of a serial port or a parallel port into a computer system for processing and intelligent recognition.

This embodiment adopts the beamlines U12B ignited by the Light Source of the National Synchrotron Radiation Laboratory, Hefei (storage ring energy: 800 Mev), which are dedicated to soft X-ray microimaging research.

The synchrotron radiation soft X-ray lung cancer microscopic image signal is an analog signal. However, since the signal is a certain magnitude of voltage, current or resistance changes, it must be conditioned by amplification, buffering or calibration before converted to a digital signal, so as to be suitable for being input to a subsequent signal collection unit. In short, an image signal conditioning unit converts the analog signal of the soft X-ray lung cancer microscopic image to a standard signal that can be recognized by collection equipment through operations such as amplification and filtering.

An image collection unit for synchrotron radiation soft X-ray lung cancer microimaging is equivalent to an analog/digital converter (ADC) which converts the image analog signal to a digital signal for data collection, control process, execution, calculation, display, readout or other purposes. Moreover, the image needs to meet a certain sampling rate and control conditions before being sent to a computer for digital processing.

The synchrotron radiation soft X-ray lung cancer microimaging analysis and recognition comprises image pre-processing, image segmentation analysis, overlapped cell reconstruction, cell feature extraction, cell feature classification (neural network recognition, etc.) and diagnosis result output.

The computer intelligent diagnosis processing part of synchrotron radiation soft X-ray lung cancer microimaging has the advantage that it can automatically recognize a cell image with the accuracy equal or approach to a lung cancer cell diagnosis conducted by pathologists. This part focuses on the design and realization of a lung cancer diagnosis system, whose principle is as follows: the cell image is segmented, regions where cells are present are extracted, overlapped cells are separated and reconstructed, feature extraction is performed to segmented independent cells, and tools such as a neural network are used for intelligent recognition according to extracted features, so as to provide an objective pathological diagnosis.

The projection algorithm is applied to project a collected original lung cancer color image from a three-dimensional RGB color space to a one-dimensional linear 256 level grey space; the double threshold fast segmentation method is used for the threshold segmentation of the grey image so as to obtain a good binary image. That is how the digital soft X-ray lung cancer microscopic image is preprocessed.

On the basis of image pre-processing, morphological filtering is performed to the binary image to improve the geometric shape of the cell region in the slice image. The morphological filtering can to some extent eliminate possible burrs and micropore-like noise in image collection and conversion, thus guaranteeing the accuracy in cell region segmentation.

Pseudo boundaries and outlines obtained by the segmentation of interconnected and overlapped cells and subsequently cause errors occur in cytogenesis information extraction, so, these factors must be eliminated, The chain code representation of the cell region is used for edge tracking calculation of the binary image to obtain a series of geometric shapes and textural features of the cell region, including perimeter, area, similar circle degree and rectangular degree of the cell region; then, statistical analysis is performed to the color histogram of the cell region with color slice image data, so as to obtain the color features. Image recognition is performed to segmented cell regions using such features as shape, density and texture, so as to mark the cancer cell region.

The morphological feature and color feature of the cell region are respectively taken as input vectors of an individual neural network, which are sent to an integrated neural network for classification and recognition of lung cancer cells. System integration is subject to the output of neural networks at various levels. Rules or neural networks can be used to rapidly and accurately determine whether the subject suffers from lung cancer, producing diagnosis results at last.

The final system adopts a GUI interface, uses a software platform to analyze and recognize biological samples. It is conveniently to perform different operations to the soft X-ray lung cancer microscopic image, and provides conclusions such as category.

Finally, it is noted that, obviously, the above-mentioned embodiments are only examples to clarify this invention, and not be considered as limiting the implementation mode. For those with ordinary knowledge and skills in the art, any variations or modifications to the embodiments can also be made on the basis of the above description. All the implementation modes need not, and can not, be exhausted herein. Obvious variations or modifications extended herefrom are still within the scope of protection of this invention.

The invention claimed is:

1. A method for utilizing soft X-ray microimaging for cancer cell image recognition, comprising the steps of: sample preparation; pathological examination; soft X-ray imaging; and analysis and recognition, wherein the sample preparation comprises the following steps:
cutting a pathological tissue cell sample into ultra-thin sliced samples with 2-3 nm thickness;
placing the ultra-thin sliced samples onto a surface of water in a water tank with 38° C.-40° C. to enable the samples to quickly and uniformly unfold into a planar shape on the water surface;
taking out the ultra-thin sliced samples floating and flattening in the water tank with an electron microscope copper grid; and
then placing the grid on a piece of absorbent paper for dehydration and drying, wherein the pathological examination comprises the following steps:
the electron microscope copper grid ultra-thin sliced samples are sent to a pathological examination department, in which said samples will be subject to a pathological examination under an optical microscope;
after a cancer cell is identified, a field of view is selected and fixed for observing the cancer cell; and
an optical microscopic picture of the cancer cell enlarged by 100 times is shot under the optical microscope, wherein the soft X-ray imaging comprises the following steps: the electron microscope copper grid ultra-thin sliced samples are sent to a synchrotron radiation experimental station, in which the samples are subject to scan diffraction by synchrotron radiation soft X-rays microscopic beamlines and imaged on the photoresist, then, observing the samples with microscopic transmission and shooting a soft X-ray microscopic image, wherein a wavelength of the soft X-rays microscopic beamlines ranges from 1.0 to 10.0 nm; a water window of soft X-ray microscopy for exposure of biological samples is made of silicon nitride with different thickness options, of which the thinnest is 20 nm, wherein the analysis and recognition comprises the following steps:
after the synchrotron radiation X-ray microscopic imaging of the cancer cell, image signal conditioning is first conducted;
image signal collection is then conducted for digital sampling; and
finally, a digital signal is sent in the form of a serial port or a parallel port into a computer system for processing and intelligent recognition, wherein the synchrotron radiation soft X-ray microscopic image signal is an analog signal, it must be conditioned by amplification, buffering or calibration before converted to a digital signal, so as to be suitable for being input to a subsequent signal collection unit, wherein the image signal collection comprises image pre-processing, image segmentation analysis, overlapped cell reconstruction, cell feature extraction, cell feature classification and diagnosis result output, and wherein the image pre-processing comprises grey level transformation, histogram adjustment, cell pre-processing, nucleus pre-processing and lymphocyte removal;
said grey level transformation is a process that utilizes a formula for conversion between a color image and a grey image to convert a cell image to grey level format, so as to facilitate subsequent processing;

said histogram adjustment is a process that indirectly enhances contrast by stretching or equalizing a histogram;

said cell pre-processing comprises contrast adjustment, binarization and edge detection;

said lymphocyte removal comprises erosion, expansion and logical processing, in order to obtain the image of a cell without lymphocyte;

said image segmentation analysis comprises threshold-based segmentation, structural morphological image processing of cell tissues, and edge detection;

said threshold-based segmentation is for cell outline segmentation;

said structural morphological image processing of cell tissues involves outline tracking, erosion and expansion;

said edge detection eliminates noise caused by inter-cell adjacency, lest the subsequent extraction of cell feature values is affected;

said overlapped cell reconstruction is a process that prevents errors in cytogenesis information extraction, caused by pseudo boundaries and outlines obtained by segmentation of interconnected and overlapped cells;

a nucleo-cytoplasmic ratio method or a colorimetric method is adopted for cell feature extraction;

said nucleo-cytoplasmic ratio method uses a bwareaopen function to remove small-area outlines through gradually selecting thresholds of areas of connected regions; outline difference between nucleus and cytoplasm is clearly displayed; a nucleo-cytoplasmic area ratio is calculated; for normal cells, the nucleo-cytoplasmic ratio is 1:4 or 1:6; for cancer cells, the ratio is 1:1;

said colorimetric method utilizes colorimetric characteristics of cancer cell nucleus for further classification and recognition of suspected cancer cell nucleus, given that cancer cell nucleus is normally darker than normal cell nucleus and clustering of its color components varies in a color space;

said cell feature classification and diagnosis result output method includes a BP neural network method, a support vector machine method or a decision tree method; and said BP neural network method utilizes three layers of BP network for cancer cell diagnosis, and involves extracting feature parameters according to the clinical features of a cancer cell, collecting a large number of samples to train neural networks, and utilizing trained networks for cancer cell diagnosis.

2. The method for utilizing soft X-ray microimaging for cancer cell image recognition according to claim 1, wherein the cancer cell is a lung cancer cell or an esophageal carcinoma cell.

* * * * *